(12) United States Patent
Seifert et al.

(10) Patent No.: US 11,154,286 B2
(45) Date of Patent: Oct. 26, 2021

(54) SURGICAL DEVICES FOR ACCESS TO SURGICAL SITES

(71) Applicant: GLOBUS MEDICAL, INC., Audubon, PA (US)

(72) Inventors: Jody Seifert, Birdsboro, PA (US); Sean Suh, Morganville, NJ (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 15/962,114

(22) Filed: Apr. 25, 2018

(65) Prior Publication Data

US 2018/0235593 A1 Aug. 23, 2018

Related U.S. Application Data

(63) Continuation of application No. 14/212,903, filed on Mar. 14, 2014, now Pat. No. 9,980,710.

(51) Int. Cl.
*A61B 17/02* (2006.01)
*A61B 17/34* (2006.01)

(52) U.S. Cl.
CPC ...... *A61B 17/0206* (2013.01); *A61B 17/3462* (2013.01); *A61B 17/3417* (2013.01); *A61B 2017/349* (2013.01); *A61B 2017/3458* (2013.01)

(58) Field of Classification Search
CPC ............ A61B 17/0206; A61B 17/3462; A61B 2017/349; A61B 17/3417; A61B 2017/3458; A61B 17/0218

USPC .................................................. 600/201–245
See application file for complete search history.

(56) References Cited

U.S. PATENT DOCUMENTS

| 5,618,297 | A | * | 4/1997 | Hart | A61B 17/3417 604/164.01 |
|---|---|---|---|---|---|
| 5,951,466 | A | | 9/1999 | Segermark et al. | |
| 5,976,146 | A | | 11/1999 | Ogawa et al. | |
| 6,036,638 | A | | 3/2000 | Nwawka | |
| 6,224,608 | B1 | * | 5/2001 | Ciccolella | A61B 17/3421 604/115 |
| 6,238,373 | B1 | * | 5/2001 | de la Torre | A61B 17/3417 604/246 |
| 6,432,048 | B1 | | 8/2002 | Francois | |
| 6,814,715 | B2 | | 11/2004 | Bonutti et al. | |
| 6,902,530 | B1 | | 6/2005 | Pianka | |
| 7,594,888 | B2 | | 9/2009 | Raymond et al. | |
| 2004/0054353 | A1 | | 3/2004 | Taylor | |
| 2004/0254426 | A1 | | 12/2004 | Wenchell | |
| 2007/0156024 | A1 | * | 7/2007 | Frasier | A61B 17/02 600/219 |

(Continued)

*Primary Examiner* — Eduardo C Robert
*Assistant Examiner* — Tara Rose E Carter

(57) ABSTRACT

Access devices including access ports and retractors, which enhance the working area and access to a surgical site. The access port includes a tubular body with at least one sidewall defining an interior path along the length of the tubular body. The sidewall includes a rigid portion and a flexible portion. The flexible portion is able to stretch or deform, for example, to accommodate an angled trajectory of a surgical implement. A surgical access device for retracting tissue includes a plurality of retractor blades. The outer surface of the retractor blades form a substantially circular cross-sectional configuration with a plurality of spiral ridges projecting therefrom such that advancement of the retractor into the surgical site may be improved.

14 Claims, 6 Drawing Sheets

(56) References Cited

U.S. PATENT DOCUMENTS

| | | |
|---|---|---|
| 2007/0219416 A1* | 9/2007 | Perez-Cruet ........... A61B 17/02 |
| | | 600/219 |
| 2009/0036746 A1* | 2/2009 | Blackwell .......... A61B 17/0206 |
| | | 600/219 |
| 2010/0261974 A1 | 10/2010 | Shelton, IV et al. |
| 2012/0022575 A1* | 1/2012 | Mire .................... A61B 5/4893 |
| | | 606/198 |
| 2012/0041335 A1 | 2/2012 | Clark et al. |
| 2012/0323080 A1* | 12/2012 | DeRidder .......... A61B 17/0218 |
| | | 600/208 |
| 2013/0225934 A1* | 8/2013 | Raybin ............ A61B 17/32056 |
| | | 600/214 |
| 2013/0317312 A1 | 11/2013 | Eastlack et al. |
| 2014/0005484 A1* | 1/2014 | Charles .............. A61B 17/3211 |
| | | 600/201 |

* cited by examiner

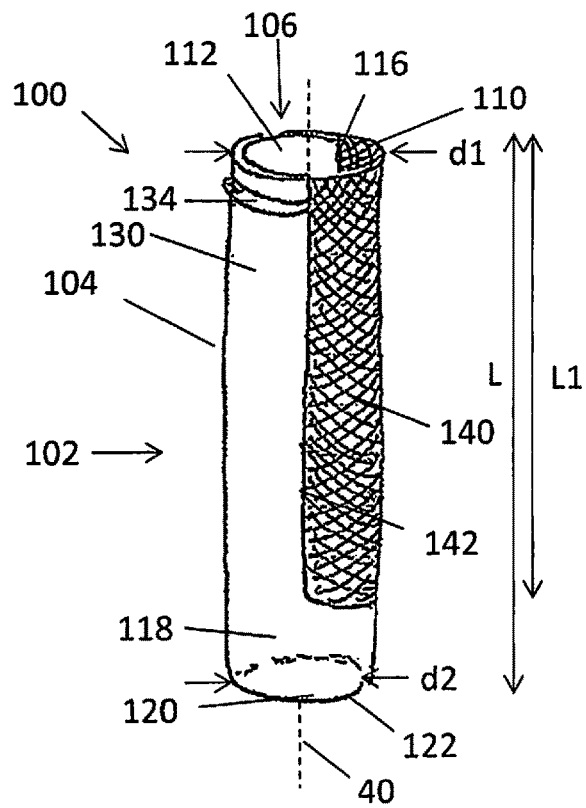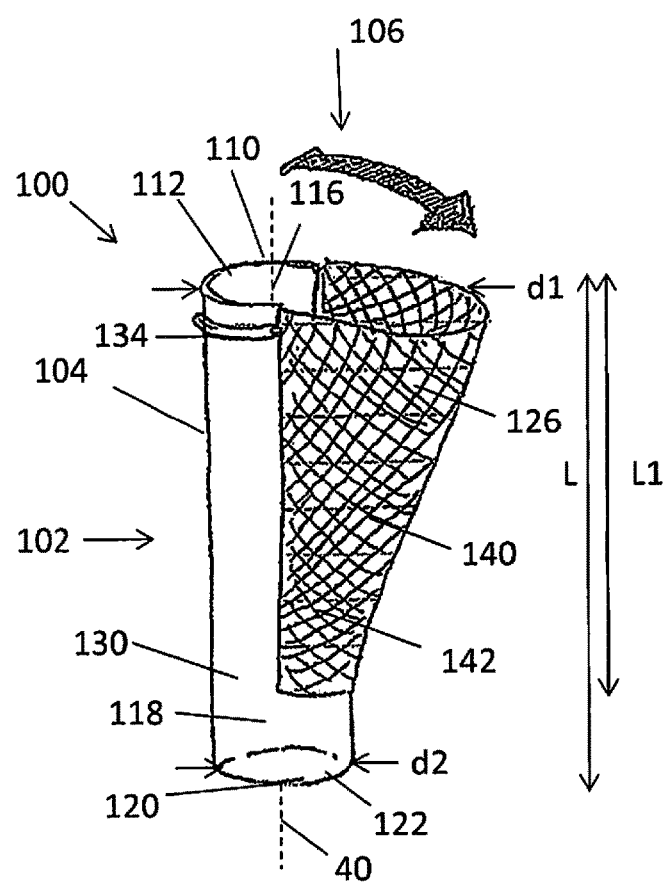

SURGICAL DEVICES FOR ACCESS TO SURGICAL SITES

CROSS-REFERENCE TO RELATED APPLICATIONS

The present application is a continuation application of U.S. patent application Ser. No. 14/212,903 filed on Mar. 14, 2014 (published as U.S. Patent Publication No. 2015-0257746), which is hereby incorporated by reference in its entirety herein.

FIELD OF THE INVENTION

The present disclosure generally relates to devices used in surgery. More particularly, the surgical devices include instruments and tools for providing access to and retraction of surgical sites.

BACKGROUND OF THE INVENTION

In surgical procedures, access ports and retractors are often used to provide access to a surgical site. In minimally invasive surgical (MIS) procedures, for example, in spinal surgery, access ports may be used to provide direct and unobstructed access to the surgical site. By way of example, one or more screws may be delivered through the access port to secure a spinal fixation device. The access port is typically rigid to aid insertion of the screws, allow for fixation and attachment to a table arm, to provide for soft tissue distraction, or other similar functions. The rigid access ports, however, can restrict or prohibit insertion of the screws or other surgical devices or instruments if the insertion path extends beyond the working area of the rigid access port. Thus, rigid access ports may not be able to accommodate an angled trajectory and/or a long length of the screws, for example.

Retractors or retractor systems are also used in a variety of different surgical procedures to provide an opening through which an operator may access the surgical site. In spinal surgeries, for example, a retractor may be used to provide the surgeon with improved access to the patient's spine. The opening created by the retractor may, for example, enable the surgeon to insert surgical instruments, devices, and the like into the body and improve visualization of the surgical site. The retractor may include blades, which may be inserted into an incision and then retracted to displace the tissue surrounding the incision down to the surgical site. Typical retractors, however, may be difficult to advance or insert into the soft tissue or may damage the surrounding tissue.

SUMMARY OF THE INVENTION

To meet these and other needs, access devices are provided, which improve the working area and access to the surgical site. In particular, access ports are provided with flexible areas designed to accommodate angled trajectories and long lengths for surgical devices and implements. The retractors are provided with retractor blades having specially designed outer surfaces configured to improve penetration and advancement of the retractor into the surgical site.

According to one embodiment, a surgical access device for providing access to a patient during surgery includes a tubular body having a first end defining a first opening configured for receiving a surgical implement, a second end defining a second opening configured for accessing the patient, a length extending from the first end to the second end, and at least one sidewall defining an interior path along the length of the tubular body. The at least one sidewall includes a rigid portion and a flexible portion. The flexible portion extends along at least a portion of the length of the tubular body. The flexible portion may be configured to stretch or deform to accommodate an angled trajectory of the surgical implement.

The flexible portion may be situated along the length of the tubular body and can replace at least a portion of a traditional rigid sidewall. The flexible portion may be configured to expand radially and/or to stretch laterally. For example, the flexible portion may extend from the first end or the second end to a distance along the length of the tubular body. For example, the flexible portion may extend to greater than 50% of the length of the tubular body. The flexible portion may encompass a portion of the outer perimeter or the entire outer perimeter along a given length of the tubular body. The flexible portion may be formed from a woven biocompatible material, such as a mesh structure, which is flexible in one or more directions.

The rigid portion comprises the remainder of the tubular body not containing the flexible portion. The rigid portion may include an annular collar, for example, positioned at the first end or the second end of the tubular body. The rigid portion may extend from the first end to the second end along the entire length of the tubular body. The flexible portion and the rigid portion may bifurcate at least a portion of the tubular body, for example, parallel to or perpendicular to a longitudinal axis of the tubular body.

The tubular body may have any suitable cross-sectional configuration designed to accommodate the surgical implements on a given angled trajectory. The tubular body may have a substantially uniform diameter along a portion of its length or its entire length. The tubular body may also include an enlarged portion. The tubular body may have a first diameter at the first end and a second diameter at the second end where the first and second diameters are not equal. For example, the first diameter may be larger than the second diameter or the second diameter may be larger than the first diameter. The tubular body may also have a third diameter positioned between the first and second ends. The third diameter may be the same or different (e.g., larger or smaller) from the first and second diameters. By way of example, the tubular body may have a shape selected from a bulbous shape, an hourglass shape, a dumbbell shape, a tapered shape, a flared shape, a funnel shape, or the like.

According to another embodiment, a surgical access device for retracting tissue includes a plurality of retractor blades each having a generally arcuate segment with a distal end, a proximal end, and an outer surface. The retractor blades are radially spaced apart to define a passage extending from the proximal end to the distal end. The retractor blades may also define at least one continuous slot between each of the retractor blades. The outer surface of the retractor blades may form a substantially circular cross-sectional configuration having a plurality of spiral ridges projecting therefrom. The spiral ridges may be configured to allow for rotational insertion of the retractor into the surgical site (e.g., in a corkscrew manner). After insertion, the retractor blades are configured to pivot away from a center line such that the passage is expandable and the tissue is retracted in response to an applied force.

The retractor blades may be fully threaded such that the spiral ridges extend from the distal end to the proximal end. In the alternative, the retractor blades may be partially threaded such that the spiral ridges extend from the distal end to a distance less than the proximal end. The retractor blades may form a beveled tip at the distal end to enhance insertion of the retractor blades into the surgical site.

According to another embodiment, a method of retracting tissue includes inserting a surgical retractor into an incision in a patient's skin by rotating the surgical retractor (e.g., like a corkscrew). After the retractor is appropriately inserted, the blades of the surgical retractor may be moved away from a center line thereof, thereby enlarging the incision and retracting the tissue.

BRIEF DESCRIPTION OF DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIGS. 5A and 5B also depict alternative embodiment of the access ports;

DETAILED DESCRIPTION OF THE INVENTION

Figure 1:
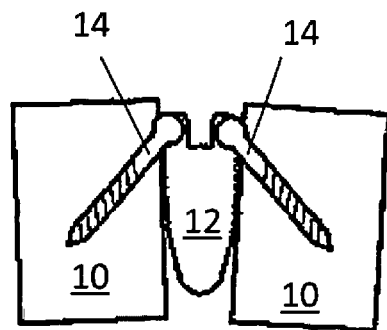
FIG. 1 depicts two vertebrae with a spacer implanted in the intervertebral disk space between the two vertebrae.

Embodiments of the disclosure are generally directed to access devices including access ports and retractors, which enhance the working area and access to the surgical site. The access devices have one or more passageways configured to receive a device, instrument, or other surgical component. The access devices may serve a number of different functions, including aiding insertion of surgical devices and implements (e.g., implants, screws, and the like), providing for soft tissue distraction, enhancing penetration and advancement of the access device into the surgical site, allowing for fixation and attachment to a table arm, and other similar functions. Suitable access devices include, but are not limited to, access ports, cannulas, sleeves, lumens, distractors, retractors, retractor systems, etc. For example, the access device may include access ports provided with flexible areas designed to accommodate angled trajectories and long lengths for surgical devices and instruments. The access device may also include retractors provided with retractor blades having specially designed outer surfaces configured to improve rotational advancement of the retractor into the surgical site.

As used herein and in the claims, the terms "comprising" and "including" are inclusive or open-ended and do not exclude additional unrecited elements, compositional components, or method steps. Accordingly, the terms "comprising" and "including" encompass the more restrictive terms "consisting essentially of" and "consisting of." It is also noted that, as used in this disclosure and the appended claims, the singular forms "a," "an" and "the" include plural referents unless the context clearly dictates otherwise. Furthermore, the words "proximal" and "distal" refer to directions closer to and further away from a reference point, respectively. For example, an operator (e.g., surgeon, physician, nurse, technician, medical professional, etc.) may insert the medical device into the patient with the tip-end (e.g., the distal end) of the device inserted inside a patient's body.

The access devices may be adapted to permit insertion through a minimally invasive procedure or micro-incision. The access devices are also especially suitable for spinal surgeries and procedures. The access devices can be subcutaneously or percutaneously inserted into a biological body of a patient, such as a vertebral body, and used to provide access to the biological body. The access devices facilitate access for other surgical instruments; for example, to remove tissue from a vertebra or intervertebral disc, insert fixation devices, such as implants, rods, plates, fasteners, and the like, inject bone graft, cement, or other types of prosthesis, etc., and secure or attach fixation devices. Thus, the access devices may be used to provide a pathway for other medical devices to be inserted into a biological body to perform surgical procedures.

Examples of surgical procedures suitable for employing the access devices described herein include, but are not limited to, insertion and securement of interbody fusion devices, bone anchors, fixation devices, including rods, plates and cables, fasteners (such as screws), artificial disks, hip stems, artificial ligaments, trochars for gastro-intestinal work, or any procedure requiring access to a patient. The access devices may be part of any suitable implant instrument used to provide access to a particular area of a patient's body. The access devices can be used to position any suitable implant, instrument and/or other device in any suitable procedure where guidance of the implant, instrument and/or device is used.

By way of example, the surgical procedure may include a spinal fixation, for example, by implanting one or more fixation devices. Referring now to the figures in which like reference numbers refer to like elements, FIG. 1 depicts two vertebrae 10 with an implant, such as an intervertebral spacer 12, implanted in the intervertebral disk space between the two vertebrae 10. The spacer 12 may be secured to the adjacent vertebrae 10 using one or more fasteners, such as one or more screws 14. Depending on the configuration of the implant or spacer 12, the screws 14 may need to be provided at an angle for proper fixation in the adjacent vertebrae 10.

Figure 2:
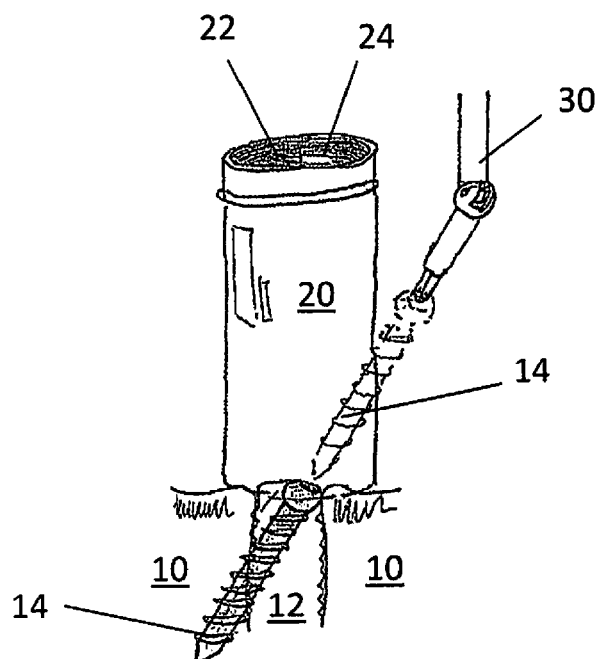
FIG. 2 depicts a traditional rigid access port and the inability to access a fixation device at the angle needed for proper attachment.

As shown in FIG. 2, traditional access devices, such as access port 20 can be restrictive in that the working area of the access port 20 is limited. The access port 20 may include an opening 22 in communication with a limited passageway 24 extending through the device. In the case of access port 20, the rigidity of the access port 20 restricts or prohibits insertion of the surgical devices in the manner required (e.g., at an angle). As is shown, surgical instrument 30 (e.g., a screw driver) is unable to access or reach screw 14 at the angle needed to secure the spacer 12 to the vertebrae 10. Due to the angled trajectory of the screw 14, the desired insertion path extends beyond the working area of the rigid access port 20 (i.e., the screw 14 and surgical instrument 30 would need to extend beyond the periphery of the access port 20). Thus, a rigid access port 20 is not able to accommodate the desired insertion path. The rigid access port 20 is also not able to deliver devices at the necessary angled trajectory or having a long length for the surgical device (e.g., screw 14) and/or the surgical instrument 30.

According to one embodiment, a surgical access device for providing access to a patient during surgery includes at least one flexible portion designed to provide an adaptable and adjustable working area. Referring now to FIGS. 3-5B, embodiments of minimally invasive access ports 100 are illustrated. The access ports 100 each include a tubular body 102 having a first end 110 defining a first opening 112 configured for receiving a surgical implement, a second end 120 defining a second opening 122 configured for accessing the patient, a length L extending from the first end 110 to the second end 120, and at least one sidewall 104 defining an interior path 106 along the length L of the tubular body 102. The sidewall 104 includes a rigid portion 130 and a flexible portion 140.

The access port 100 can be any suitable device defining a port for providing access to a surgical site. The access port 100 may include single access or multiple access points to the surgical area. For example, the tubular body 102 may define a channel or interior path 106 therethrough including a straight, curved, or any suitable shaped trajectory. The tubular body 102 is not limited to a tubular structure having closed sidewalls and can be any component that defines at least one interior path 106, including an open channel extending therethrough. The path 106 through the access port 100 may form a working channel configured to receive selected surgical instruments, such as awls, bone taps, obturators, drills, guide wires, screw drivers, and/or surgical devices, such as implants and associated structures, implants, spacers, fusion devices, rods, tethers, bone anchors, plates, cables, fasteners (e.g., screws), and the like. As used in this document, surgical implements, instruments, and devices may be used interchangeably and are intended to include any surgical instruments or devices described herein or known in the art.

The interior path 106 may be formed by the sidewall 104 (e.g., a substantially cylindrical sidewall 104). The inner and outer surfaces 116, 118 of the sidewall 104 may be smooth, rough, threaded, ribbed, or any other surface cover, which would aid in securing the access port 100 in place during the procedure, to enhance the working channel, or to improve access to the surgical site. One skilled in the art will recognize that the tubular body 102 can have any size, shape, configuration, and number of sidewalls.

The sidewall 104 includes at least one flexible portion 140. As used herein, flexible is intended to encompass any suitable materials with physical properties that allow it to move, expand, stretch, or deform when a force is applied (e.g., the force from a surgical implement). Preferably, the material is resilient such that the material returns to or near its original shape after being expanded, stretched, or deformed. The flexible material may be able to resiliently stretch or deform in one direction, two directions, or three directions (e.g., x-, y-, and/or z-directions). For example, the flexible material may provide for a three-dimensional stretching. The flexibility of the material may allow for an elongation in the range of about 5-50%, about 5-40%, about 5-30%, about 10-30%, about 10-40%, or about 20-30% in one or more directions (e.g., laterally).

Figure 4A:
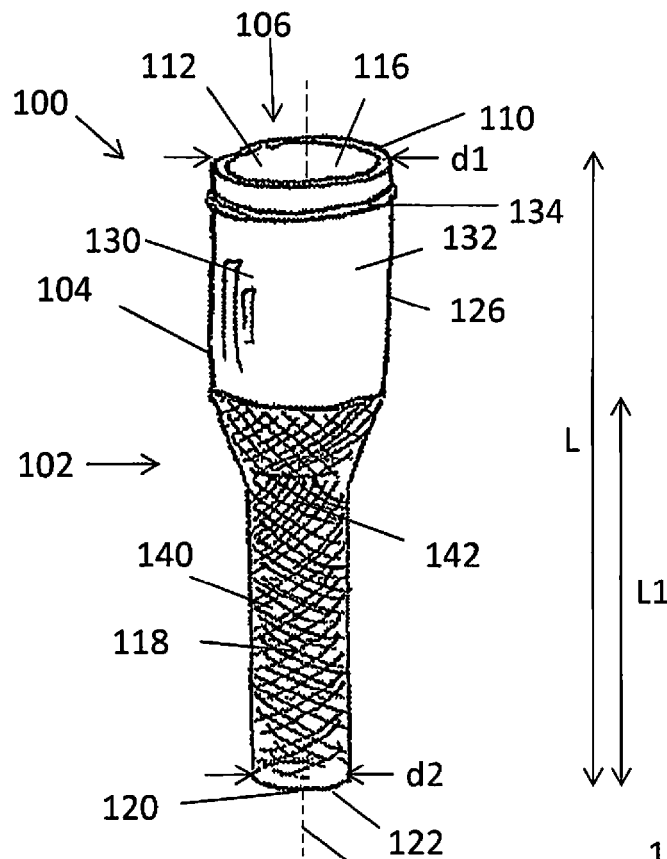
FIGS. 4A and 4B show alternative embodiments of access ports having flexible portions.
Figure 4B:
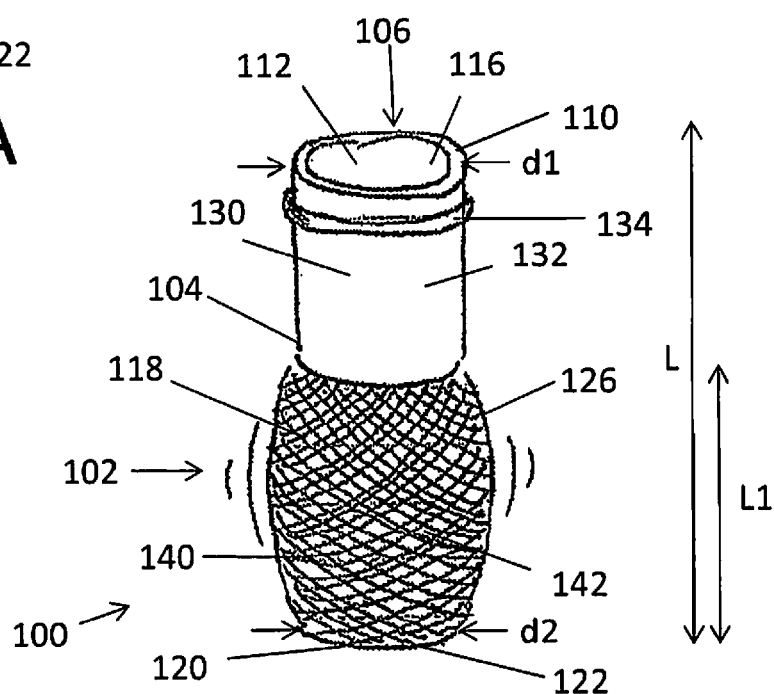

The flexible portion 140 is situated along at least a portion of the length L of the tubular body 102. The flexible portion 140 may be configured to stretch or deform, for example, to accommodate an angled trajectory of a surgical implement. The flexible portion 140 may be configured to expand radially (as shown in FIG. 4B) and/or to stretch laterally (as shown in FIG. 5B in the direction of the arrow). The flexible nature of the flexible portion 140 allows surgical implements inserted therethrough to be manipulated about their axes and thus allow a higher degree of movement of the surgical implements to orient them relative to the tissue being operated upon. After stretching or deforming under the force of the surgical implements, the flexible portion 140 may be resilient in that the material returns to its original, pre-deformed shape.

Figure 3:
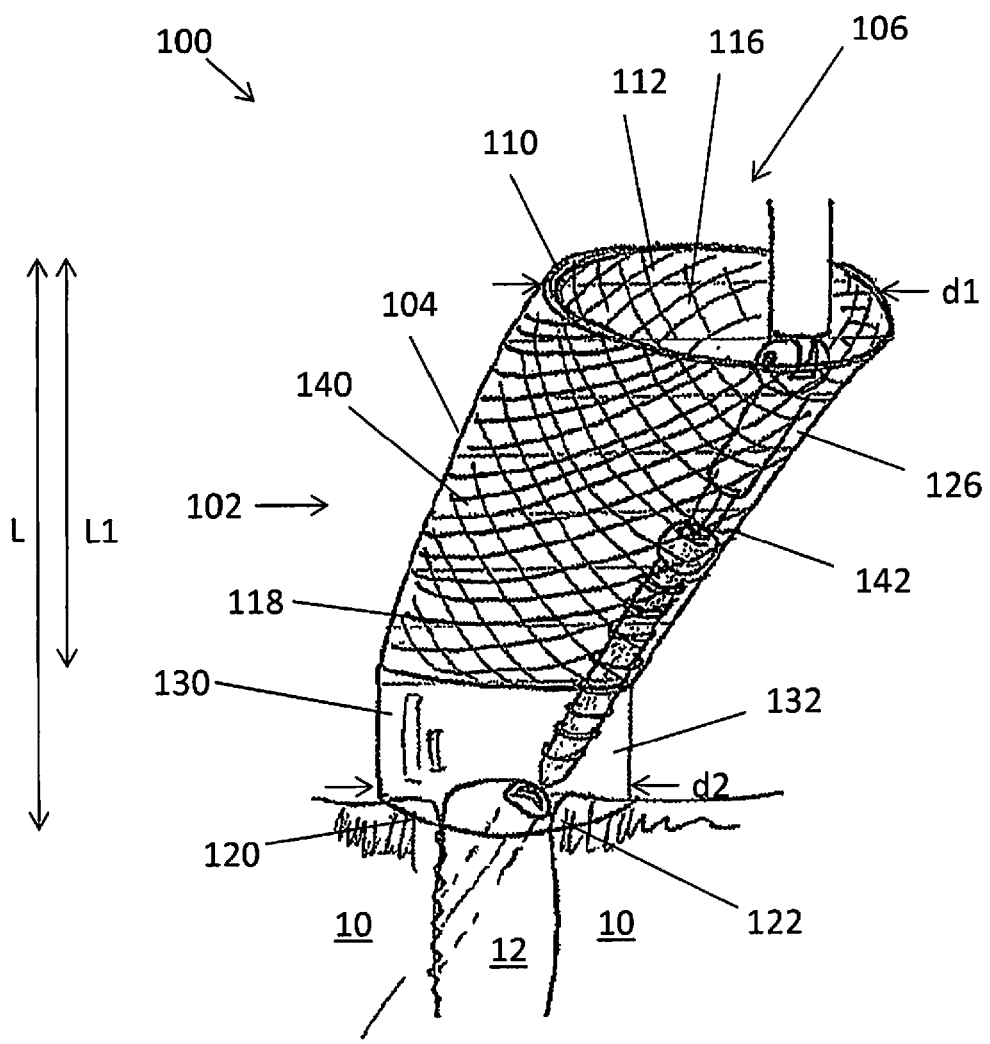
FIG. 3 provides an embodiment of an access port including a rigid portion and a flexible portion able to accommodate and access the fixation device at an angled trajectory.

The flexible portion 140 may extend along at least a portion of the length L of the tubular body 102. As depicted in FIG. 3, the flexible portion 140 may extend from the first end 110 (e.g., the insertion end) to a distance L1 along the length L of the tubular body 102. As shown in FIGS. 4A and 4B, the flexible portion 140 may extend from the second end 120 (e.g., the access end) to a distance L1 along the length of the tubular body 102. For example, the flexible portion 140 may extend to greater than 50%, greater than 60%, greater than 70%, or greater than 80% of the length L of the tubular body 102. The flexible portion 104 may range from about 50-90%, about 50-80%, about 50-70%, about 50-60%, about 60-90%, about 60-80%, or about 60-70% of the length L of the tubular body 102. Although embodiments are depicted with the flexible portion 140 extending from the first or second ends 110, 120, respectively, the flexible portion 140 may be located in any suitable location, and the access ports 100 may be oriented in any suitable direction (e.g., either the first end 110 or the second end 120 may be the insertion end and either the first end 110 or the second end 120 may be the access end of the passage way).

The flexible portion 140 may encompass a portion of the outer perimeter or the entire outer perimeter along a given distance L1 of the length L of the tubular body 102. In the embodiments shown in FIGS. 3, 4A, and 4B, the flexible portion 140 surrounds the entire periphery or circumference of the tubular body 102 along the distance L1 of the tubular body 102. In FIGS. 5A and 5B, the flexible portion 140 only surrounds a portion of the outer perimeter of the tubular body 102 along the distance L1 of the tubular body 102. For example, the flexible portion 140 may surround about 20-80%, about 20-70%, about 20-60%, about 30-80%, about 30-70%, about 30-60%, about 40-80%, about 40-70%, or about 40-60% of the circumference of the tubular body 102.

The flexible portion 140 may be formed from a web, for example, of woven material. The flexible portion may also be in the form of a mesh structure 142, which is flexible or able to elongate in one or more directions when a force is applied. In particular, the mesh structure 142 may be in the form of a web, fabric, or cloth with a construction of knitted, braided, woven, or non-woven (e.g., felt) filaments or fibers that are interlocked in such a way to create a fabric or a fabric-like material. The mesh structure 142 may be formed, for example, from monofilament or multifilament threads. The shape, form, and diameter of the threads are not particularly limited. For example, twisted thread, spun yarn, monofilament thread, multifilament thread, staple fiber, and whisker may be used. The mesh structure 142 may be formed as a net-structure, such as a square, hexagonal, or network shape, for example.

The mesh structure 142 may contain a given porosity in order to influence or enhance the flexibility of the material. Depending on the material selected, as the porosity and/or pore size increase (volumetric density decreases), the flexibility and deformability increase. Accordingly, a high porosity mesh structure 142 may be desired. For example, the mesh structure 142 may have a porosity of at least about 30%, at least about 40%, at least about 50%, at least about 65%, or at least about 75%. For example, the porosity may range from about 30-90%, about 30-80%, about 30-70%, about 30-60%, about 30-50%, about 40-90%, about 40-80%, about 40-70%, about 40-60%, about 40-50%, about 50-90%, about 50-80%, or about 50-75%. Porosity refers to the voids or pore volume of the mesh structure 142 and is the converse of the volumetric density, which is the amount, by volume, of fibers per unit volume of the mesh structure 142. Accordingly, porosity (%)=100%–volumetric density (%). The porosity or volumetric density may vary slightly from region to region of the mesh structure 142 and it is sufficient if the average value over the entire cross-section falls within the foregoing values.

The sidewall 104 also includes at least one rigid portion 130. The rigid portion 130 is a rigid or substantially rigid material, which is capable of substantially holding or retaining its shape when a force is applied. The rigid portion 130 comprises the remainder of the tubular body 102 not containing the flexible portion 140. As shown in FIGS. 3, 4A, and 4B, the rigid portion 130 may include a ring or annular collar 132, for example, positioned at the first end 110 or the second end 120 of the tubular body 102. As shown in FIGS. 5A and 5B, the rigid portion 140 may extend from the first end 110 to the second end 120 along the entire length L of the tubular body 102. The rigid portion 140 may also include a combination of the annular collar 132 and one or more portions extending along the length L of the tubular body 102.

The flexible portion 140 and the rigid portion 130 may bifurcate at least a portion of the tubular body 102. For example, the tubular body 102 may be bifurcated in a manner parallel to or perpendicular to a longitudinal axis 40. For example, FIGS. 3, 4A, and 4B depict access ports 100 bifurcated along a plane perpendicular to the longitudinal axis 40, and FIGS. 5A and 5B depict access ports 100 bifurcated along a plane parallel to the longitudinal axis 40 for the distance L1.

The rigid portion 130 of the access port 100 is helpful for port insertion and for attachment and fixation in the surgical setting. In particular, the rigid portion 130 of the access port 100 may include a projection, attachment, or other mechanism for rigidly attaching or affixing the access port 100 to a table arm, for example, for securing the position of the access port 100 during the surgical procedure. The rigid portion 130 may include, for example, a ridge 134 along at least a portion of its circumference designed to engage a table arm.

The tubular body 102 may have any suitable cross-sectional configuration designed to accommodate the surgical implements, for example, on a given angled trajectory. The tubular body 102 may have a substantially uniform diameter along a portion of length L or its entire length L. As shown in FIG. 5A, the access port 100 can have a substantially uniform diameter along its entire length L in its relaxed state. For example, the first diameter d1 at the first end 110 may be equivalent to the second diameter d2 at the second end 120 of the access port 100 (and along the entire length L). FIG. 5B depicts access port 100 when a force is applied to the flexible portion 140 sufficient to stretch or deform the flexible portion 140. In particular, a lateral force may be applied in the direction of the arrow designed to allow for an angled trajectory of one or more surgical implements. Thus, the force may alter the geometry of the access port 100 such that the first diameter d1 is now greater than the second diameter d2 in the expanded configuration. After the force is removed, the flexible portion 140 may return to the relaxed state having a uniform diameter along its length L as shown in FIG. 5A.

The tubular body 102 may have first and second diameters d1, d2, which are not equal. For example, the first diameter d1 may be larger than the second diameter d2 or the second diameter d2 may be larger than the first diameter d1. The tubular body 102 may also have one or more intermediate diameters (e.g., a third diameter) positioned between the first and second ends 110, 120. The intermediate diameter or third diameter may be the same or different (e.g., larger or smaller) from the first and second diameters d1, d2 to provide for a tubular body 102 having varying widths or diameters along its length L.

The tubular body 102 may also include an enlarged portion 126 in its relaxed state or expanded state. As shown in FIGS. 3 and 4A, the enlarged portion 126 may include a portion of the tubular body 102 proximate to the first end 110. As shown in FIG. 4B, the enlarged portion 126 may include a portion of the tubular body 102 near the second end 120. The enlarged portion 126 may include the flexible portion 140 (FIGS. 3 and 4B) and/or the rigid portion 130 (FIG. 4A). Similarly, the tubular body 102 may also include one or more narrowed regions and/or transition regions, for example.

The tubular body 102 may be of any suitable size and shape designed to improve access to the working area of the surgical site. For example, the tubular body 102 may have a shape selected from a bulbous shape, an hourglass shape, a dumbbell shape, a tapered shape, a flared shape, a funnel shape, or the like. Although depicted as a substantially tubular structure, the access port 100 can be a variety of different shapes and size, such as having round, square, rectangular, triangular, elliptical, or octagonal inner and/or outer perimeters. Thus, the access port 100 can have any suitable cross-section and is not limited to the substantially cylindrical cross-sections shown in the illustrative embodiments.

The surgical access port 100 including the flexible portion 140 and the rigid portion 130 can be formed of any suitable surgical material. Preferably, the surgical access port 100 is comprised of one or more physiologically compatible or biocompatible materials, for example, that have the property or characteristic of not generating injury, toxicity, or immunological reaction to living tissues. Suitable physiologically compatible or biocompatible materials include, but are not limited to plastics, such as polyether ether ketone (PEEK); metals, such as surgical stainless steel, titanium, and other materials known in the art. The surgical access port 100 may also be made of a combination of suitable materials.

With regard to the flexible portion 140, malleable, bendable, or flexible materials, including metals, plastics, inorganics, and composites, known in the art may be used. Metals may include, for example, titanium, titanium alloys, surgical stainless steel, nickel titanium alloys, and shape memory alloys.

Plastics may include, for example, polyesters, such as polyethylene terephthalate and polybutylene terephthalate; aliphatic polyesters; polyethers; polyether-esters, such as polybutester; polyamides, such as nylon and polycaprolactam; polyamines; polyimines; polyurethanes; acrylic polymers and copolymers; modacrylics; vinyl halide polymers and copolymers, such as polyvinyl chloride; polyvinyl alcohols; polyvinyl ethers, such as polyvinyl methyl ether; polyvinylidene halides, such as polyvinylidene fluoride and polyvinylidene chloride; polyacrylonitrile; polyaryletherketones; polyvinyl ketones; polyvinyl aromatics, such as polystyrene; polyvinyl esters, such as polyvinyl acetate; copolymers of vinyl monomers with each other and olefins, such as etheylene-methyl methacrylate copolymers, acrylonitrile-styrene copolymers, ABS resins, and ethylene-vinyl acetate copolymers; alkyd resins; polycarbonates; polyoxymethylenes; polyphosphazine; polyimides; epoxy resins; aramids, rayon; rayon-triacetate; spandex; silicones; and combinations thereof.

Inorganics may include, for example, biocompatible inorganic fibers such as carbon fibers, graphite fibers, glass fibers, silica fibers, zirconia fibers, apatite fibers, and material fibers such as stainless steel fibers, titanium fibers, alumina fibers, boron fibers, etc. As discussed above, these fibers may be formed into a web, fabric, cloth, or the like.

With regard to the rigid portion 130, a biocompatible plastic, like polyether ether ketone (PEEK), polyetherketoneketone (PEKK), ultra-high molecular weight (UHMW) polyethylene, or other polymers and plastics known in the art which are physiologically compatible may be used. A biocompatible metal, such as stainless steel, titanium, titanium alloys, surgical steel, and metal alloys may also be used, for example. Any other materials or a combination that are physiologically compatible may also be used, such as bone or plastic.

According to another embodiment, a surgical access device for retracting tissue includes a retractor 200 or retractor system. Referring to FIGS. 6-9, embodiments of minimally invasive retractors 200 and/or the retractor blades 202 are illustrated. The retractor 200 includes a plurality of retractor blades 202 each having a generally arcuate segment 204 with a distal end 220 (e.g., for insertion into the surgical site), a proximal end 210 (e.g., for attachment to arms 230 or a frame), an inner surface 216, and an outer surface 218. The retractor blades 202 are radially spaced apart to define a passage 206 extending from the proximal end 210 to the distal end 220. The outer surface 218 of all of the retractor blades 202 combined may form a substantially circular cross-sectional configuration. The outer surface 218 has a plurality of spiral ridges 224 projecting therefrom configured to facilitate insertion in a rotational manner. The retractor blades 202 are also configured to pivot away from a center line 42 such that the passage 206 is expandable in response to an applied force such that the tissue in the surgical site is retracted.

According to yet another embodiment, a method of retracting tissue includes inserting the surgical retractor 200 into an incision in a patient's skin by rotating the surgical retractor 200 (e.g., in a corkscrew manner). After the retractor 200 is appropriately inserted, the blades 202 of the surgical retractor 200 may be moved away from a center line 42 thereof, thereby enlarging the incision.

The retractor 200 may be in the form of a self-tapping retractor, which enables the retractor 200 to at least partially corkscrew into an opening instead of forcing the entire retractor 200 into the surgical opening or incision. In other words, a portion of retractor 200 (e.g., distal end 220) may be inserted and plunged at least partially into the biological body and then the remainder of the retractor 200 can be threadably turned or screwed into the biological body, for example, when a torque is applied. By rotatably screwing the retractor 200 into the biological body, insertion time and the effort required to insert the retractor 200 into the biological body can be greatly reduced. The raised ridges 224 may contain at least one cutting edge to facilitate insertion of the retractor blades 202 when a torque is applied.

Figure 9:
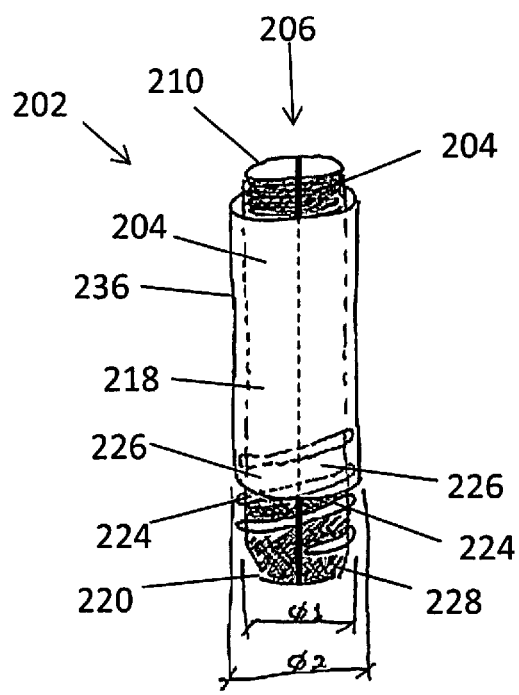
FIG. 9 depicts another embodiment of a threaded retractor.

The retractor blades 202 may include a beveled tip 228 at the distal end 220 to enhance insertion of the retractor blades 200 into the surgical site. For example, the beveled tip 228 may be tapped into the site, for example, with a plunge force or by using a mallet or other device which applies a force, e.g., non-rotational force, to the retractor blades 202. After the initial insertion, the retractor blades 202 may be advanced through rotation to control the position or depth of the retractor blades 202. The retractor blades 202 may be advanced through a sleeve or cannula 236, for example, as shown in FIG. 9, where the diameter Ø1 the retractor blades 202 is smaller than the diameter Ø1 of the sleeve or cannula 236.

Figure 7:
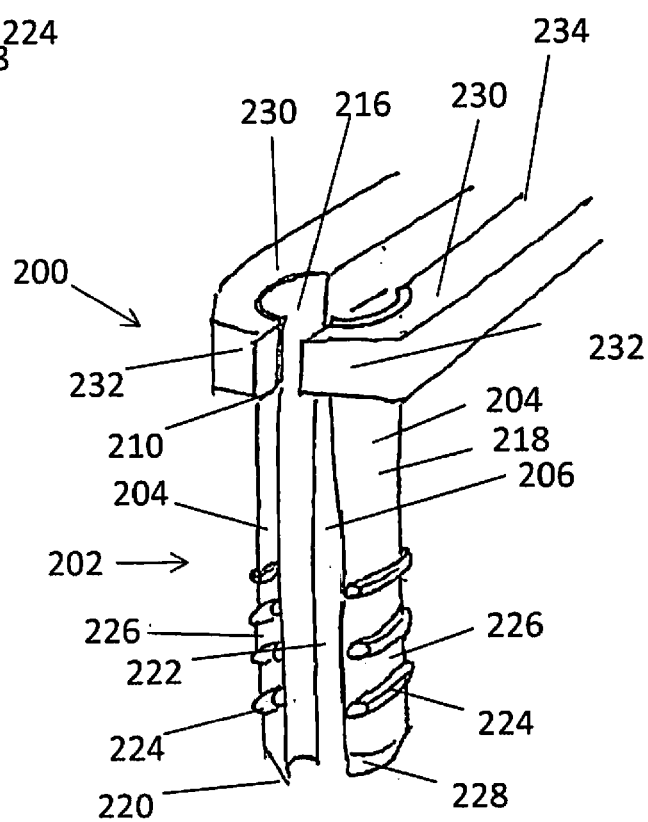
FIG. 7 shows one embodiment of a retractor.
Figure 8:
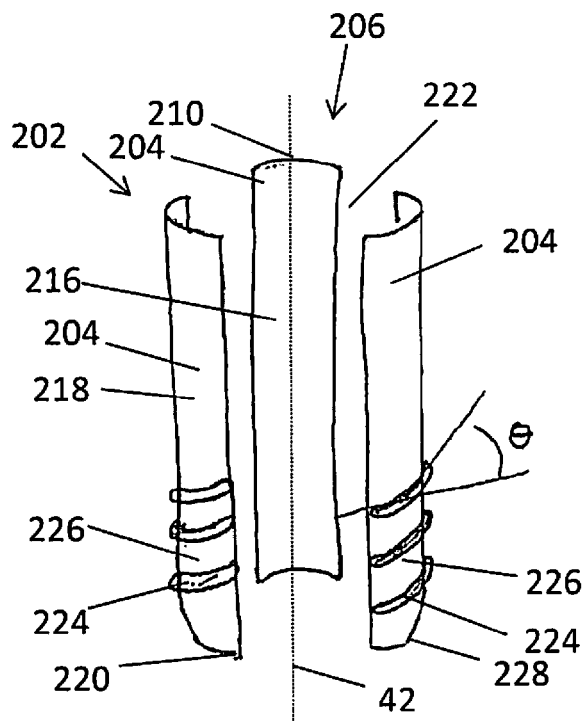
FIG. 8 shows an alternative embodiment of the retractor blades.

The retractor blades 202 may form generally curved or arcuate structures 204 that cooperate to define segments of a substantially circular cross-sectional configuration. The retractor blades 202 may define segments of a substantially c-shape, thereby providing sufficient stiffness or rigidity such that retractor blades 202 resist bending from the counter forces of the retracted tissues. Depending on the number of retractor blades 202, each retractor blade 202 may have an arcuate configuration that is less than about 180° (e.g., two retractor blades 202), less than about 120° (e.g., three retractor blades 202), less than about 90° (e.g., four retractor blades 202), less than about 72° (e.g., five retractor blades 202), etc. For example, FIG. 7 depicts two retractor blades 202 where each retractor blade 202 has an arcuate configuration of about 180° and FIG. 8 depicts three retractor blades 202 where each retractor blade has an arcuate configuration of about 120°. Although the retractor blades 202 are depicted as arcuate structures 204, the retractor blades 202 may be of any suitable size, shape, cross-section (e.g., convex, square, rectangular), or other configurations known in the art.

Figure 6:
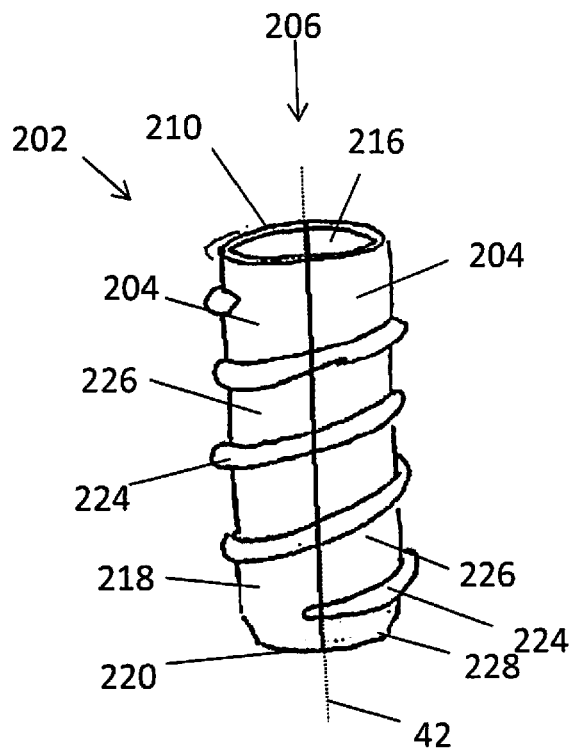
FIG. 6 shows an embodiment of retractor blades having an outer surface designed to improve access to the surgical site.

Before, during, or after insertion, the retractor blades 202 may be in contact with one another or may be spaced apart. As shown in FIGS. 6 and 9, at least a portion of the retractor blades 202 may be in contact with one another to form a substantially closed passage 206 extending from the proximal end 210 to the distal end 220. As shown in FIGS. 7 and 8, the retractor blades 202 may be spaced apart from one another to define a passage 206 extending from the proximal end 210 to the distal end 220 and one or more slots 206 between each of the respective blades 202. In particular, the retractor blades 202 may be radially spaced apart to define one or more continuous slots 222 along a substantial portion or the entire length of the retractor blades 202.

The outer surface 218 of the retractor blades 202 include one or more raised ridges 224 that extend away from the outer surface 218 (i.e., radially outward). As illustrated in FIGS. 6-9, each ridge 224 at least partially spirals about the center line 42 or longitudinal axis and/or extends angularly along the length of the outer surface 218 of the retractor blades 202. The raised ridges 224 may be separated by one or more grooves 226. The ridges 224 may be straight or curved. In addition, the ridges 224 may be continuous or segmented. Preferably, the ridges 224 are integral and continuous with the retractor blades 202 (i.e., one-piece). When the blades 202 are combined or closed together, the raised ridges 224 may form a substantially helical thread along the periphery of the outer surface 218 of the retractor blades 202. The helical thread may be right or left handed, for example.

As shown in FIG. 8, the ridges 224 may be pitched at an angle θ relative to an axis substantially perpendicular to the center line 42 of the retractor blades 202. The angle θ or pitch may range from about 0 to 90 degrees, 5 to 75 degrees, 5 to 45 degrees, 10 to 80 degrees, 10 to 60 degrees, 15 to 50 degrees, 15 to 30 degrees, 20 to 60 degrees, 30 to 50 degrees, or 45 to 90 degrees, and all sub-ranges therebetween. For example, the angle θ or pitch of the ridges 224 may be approximately 0, 10, 20, 30, 40, 50, 60, 70, 80, or 90 degrees, or any other angle θ or pitch as would be suitable to rotatably insert the retractor blades 202. The shape or angle θ of the ridges 224 may be selected to facilitate insertion of the retractor blades 202 without damaging the integrity of the surrounding tissue.

Each ridge 224 may have the same height, width, length, and angle θ or pitch relative to one another. In certain embodiments, the ridges 224 may vary from other ridges 224 with respect to height, width, length, and/or angle θ or pitch. In some embodiments, the height, width, and angle θ or pitch may be constant or variable along each ridge 224. All of these parameters of ridges 224 may impact torsion, penetration, retractor effectiveness, and/or other parameters.

The ridges 224 may extend along the entire length of the retractor blades 202 or only a portion of the length of the retractor blades 202. In particular, the retractor blades 200 may be fully threaded such that the spiral ridges 224 extend from the distal end 220 to the proximal end 210. In the alternative, the retractor blades 202 may be partially threaded such that the spiral ridges 224 extend from the distal end 220 to a distance less than the proximal end 210. In certain embodiments, the length of the ridges 224 may extend from about 1-100 percent, 1-50 percent, 50-100 percent, 25-50 percent, 50-75 percent, 5-40 percent, 10-30 percent, and all sub-ranges therebetween, of the length of the retractor blades 202. For example, the ridges 224 may extend about 10, 20, 30, 40, 50, 60, 70, 80, 90, or 100 percent, or any other percent of the length of the retractor blades 202.

The number of ridges 224 on the outer surface 218 may be of any suitable amount or quantity. For example, larger retractor blades 202 and/or closer ridges 223 with smaller grooves 226 positioned therebetween may allow for a greater number of ridges 224, and conversely, smaller retractor blades 202 and/or further spaced apart ridges 223 with larger grooves 226 may allow for a smaller number of ridges 224. Depending on the size and shape of the retractor blades 202 and the ridges 224, the number of ridges 224 may range, for example, from about 1-200, about 1-50, about 1-10, about 1-5, and all sub-ranges therebetween. It will be understood that when the arcuate segments 204 are combined together, the ridges 224 may appear as one continuous spiral (e.g., FIG. 6).

The retractor blades 202 may be attached or affixed to any suitable arms 230, handles, frames, devices, or the like known in the art. As shown in FIG. 7, the proximal end 210 of each of the retractor blades 202 may be affixed to the distal end 232 of one or more arms 230. The arm 230 includes a proximal end 234 which may be affixed to another device or mechanism or may include a handle (not shown) such that an operator is able to maneuver the retractor blades 202. The retractor blades 202 may be mounted to a retractor frame, for example, as exemplified in U.S. Pat. No. 8,353,826, which is hereby incorporated by reference in its entirety for all purposes. The retractor 200 may further include one or more hinges, cranks, or the like (not shown), and/or may be configured to engage a variety of different tools, such as wrenches or screwdrivers, to facilitate the desired movement of the retractor blades 202.

After the retractor blades 202 have been inserted into the surgical space, for example, by threadably turning or rotatably screwing the retractor 200, the passage 206 and the slots 222 are expandable in order to retract and expose the patient's tissue. In particular, the retractor blades 202 may move or pivot away from the center line 42 in response to one or more applied forces. For example, the retractor blades 202 may pivot at a hinge (not shown) in response to manual forces applied by the surgeon. The retractor blades 202 may pivot away from the center line 42 (i.e., radially outwards) in order to create a larger opening through the passage 206 and act to retract the surrounding tissue at the selected surgical site. The movement of the retractor blades 202 may include polyaxial motion, for example, to allow the retractor 200 to expand medial-laterally, cephalad-caudally, or both. Surgeon preference will dictate the need for one or more stages of dilators or scalpel blades to aid in expanding the wound before introducing the retractor 200. Normal surgical techniques may also be used to close any incisions.

The retractors 200 including the retractor blades 202 may be formed from any suitable materials known in the art and may include any of the materials discussed for the access ports 100. In addition, the access devices described herein may be sterilized by any suitable methods including, but not limited to, autoclaving, ethylene oxide, radiation, cold sterilization (e.g., hydrogen peroxide plasma), immersion sterilization, or a combination thereof.

The access devices may serve a number of different functions, for example, including aiding insertion of surgical devices and implements (e.g., implants, screws, and the like), providing for soft tissue distraction, enhancing penetration and advancement of the access device into the surgical site, allowing for fixation and attachment to a table arm, and other similar functions. The access devices are adapted to permit insertion through minimally invasive procedures, and are especially suitable for spinal surgeries and procedures. By way of example, the spinal surgeries may include, but are not limited to, insertion of vertebral fusion and fixation devices, including rods, plates, cables, bone anchors, fasteners, such as screws, and the like, or any procedure requiring surgical access to a patient.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration.

What is claimed is:

1. A surgical access device for retracting tissue comprising:
 a plurality of retractor arms;
 a plurality of retractor blades each having an arcuate segment with a distal end, a proximal end, a middle region in between the proximal end and the distal end, and an outer surface, the plurality of retractor blades are radially spaced apart to define a passage extending from the proximal end to the distal end, the outer surface of the plurality of retractor blades forming a substantially circular cross-sectional configuration having a plurality of spiral ridges projecting therefrom, wherein the plurality of retractor blades are partially threaded such that the plurality of spiral ridges extend from the distal end to the middle region, wherein the proximal end of each one of the plurality of retractor blades is configured to couple to each one of the plurality of retractor arms, wherein each one of the retractor blades is configured to move away from a center line such that the passage is expandable in response to movement of at least one retractor arm, wherein the passage has a uniform diameter proximal end to the distal end when the plurality of retractor blades are in a closed position, wherein the plurality of retractor blades includes at least three retractor blades and wherein the passage extending from the proximal end to the distal end is continuous and extends along a substantial portion of the entire length of each of the at least three retractor blades, and wherein the at least three retractor blades are configured to be received in a cannula prior to retracting tissue.

2. The device of claim 1, wherein the plurality of retractor blades are self-tapping.

3. The device of claim 2, wherein the plurality of retractor blades have a beveled tip at the distal end.

4. The device of claim 1, wherein the plurality of spiral ridges is separated by one or more grooves.

5. The device of claim 4, wherein the plurality of spiral ridges are straight.

6. The device of claim 4, wherein the plurality of spiral ridges are curved.

7. The device of claim 4, wherein the plurality of spiral ridges form a helical thread around the outer surface.

8. A method of retracting tissue comprising:
inserting a surgical retractor into an incision in a patient's skin by rotating the surgical retractor;
wherein the surgical retractor comprises:
a plurality of retractor arms;
a plurality of retractor blades each having a arcuate segment with a distal end, a proximal end, a middle region in between the proximal end and the distal end, and an outer surface, the plurality of retractor blades are radially spaced apart to define a passage extending from the proximal end to the distal end, the outer surface of the plurality of retractor blades forming a substantially circular cross-sectional configuration having a plurality of spiral ridges projecting therefrom, wherein the plurality of retractor blades are partially threaded such that the plurality of spiral ridges extend from the distal end to the middle region, wherein the proximal end of each one of the plurality of retractor blades is configured to couple to each one of the plurality of retractor arms, wherein each one of the plurality of retractor blades is configured to move away from a center line such that the passage is expandable in response to movement of at least one retractor arm, and wherein the passage has a uniform diameter proximal end to the distal end when the plurality of retractor blades are in a closed position, and moving the at least one blade of the surgical retractor away from a center line thereof, thereby enlarging the incision, wherein the plurality of retractor blades includes at least three retractor blades and wherein the passage extending from the proximal end to the distal end is continuous and extends along a substantial portion of the entire length of each of the at least three retractor blades, and wherein the at least three retractor blades are configured to be received in a cannula prior to retracting tissue.

9. The method of claim 8, wherein the plurality of retractor blades are self-tapping.

10. The method of claim 9, wherein the plurality of retractor blades have a beveled tip at the distal end.

11. The method of claim 8, wherein the plurality of spiral ridges is separated by one or more grooves.

12. The method of claim 11, wherein the plurality of spiral ridges are straight.

13. The method of claim 11, wherein the plurality of spiral ridges are curved.

14. The method of claim 11, wherein the plurality of spiral ridges form a helical thread around the outer surface.

* * * * *